(12) United States Patent
Kaizik et al.

(10) Patent No.: US 6,407,295 B1
(45) Date of Patent: Jun. 18, 2002

(54) PROCESS FOR PREPARING HIGHER OXO ALCOHOLS FROM OLEFIN MIXTURES

(75) Inventors: Alfred Kaizik; Bernhard Scholz; Walter Toetsch, all of Marl; Martin Trocha, Essen; Wilfried Bueschken, Haltern; Franz Nierlich, Marl, all of (DE)

(73) Assignee: Oxeno Olefinchemie GmbH, Marl (DE)

( * ) Notice: Subject to any disclaimer, the term of this patent is extended or adjusted under 35 U.S.C. 154(b) by 0 days.

(21) Appl. No.: 09/396,402

(22) Filed: Sep. 15, 1999

(30) Foreign Application Priority Data

Sep. 16, 1998 (DE) .......................... 198 42 371

(51) Int. Cl.$^7$ ..................... C07C 29/16; C07C 31/125
(52) U.S. Cl. ........................ 568/883; 568/840
(58) Field of Search .................... 568/840, 883

(56) References Cited

U.S. PATENT DOCUMENTS

| | | | |
|---|---|---|---|
| 4,684,750 A | * 8/1987 | Kessen et al. | 568/883 |
| 4,968,849 A | * 11/1990 | Lueken et al. | 568/881 |
| 5,675,045 A | 10/1997 | Bueschken et al. | 568/881 |
| 5,728,891 A | 3/1998 | Bueschken et al. | 568/376 |
| 5,756,856 A | 5/1998 | Bueschken et al. | 568/462 |
| 5,831,135 A | 11/1998 | Bueschken et al. | 568/881 |

FOREIGN PATENT DOCUMENTS

| | | |
|---|---|---|
| DE | 1 935 900 | 2/1971 |
| DE | 32 32 557 | 3/1983 |
| EP | 0 183 545 | 6/1986 |
| EP | 0 326 674 | 8/1989 |
| EP | 0 850 905 | 7/1998 |
| FR | 2 322 119 | 3/1977 |

OTHER PUBLICATIONS

J. Falbe, pp. 95–123 and 164–165, "New Syntheses with Carbon Monoxide," 1980.
Encyclopedia of Chemical Technology, vol. 17, pp. 902–918, OXO Process, 1996.

* cited by examiner

Primary Examiner—Peter O'Sullivan
(74) Attorney, Agent, or Firm—Oblon, Spivak, McClelland, Maier & Neustadt, P.C.

(57) ABSTRACT

The invention relates to a process for preparing higher oxo alcohols from mixtures of isomeric olefins having from 5 to 24 carbon atoms by hydroformylation in the presence of a catalyst at elevated temperature and at elevated pressure, in which the hydroformylation is carried out in one stage, the olefin conversion rate for one pass is restricted to from 40 to 90% to produce a reaction mixture, and the reaction mixture is selectively hydrogenated.

21 Claims, 1 Drawing Sheet

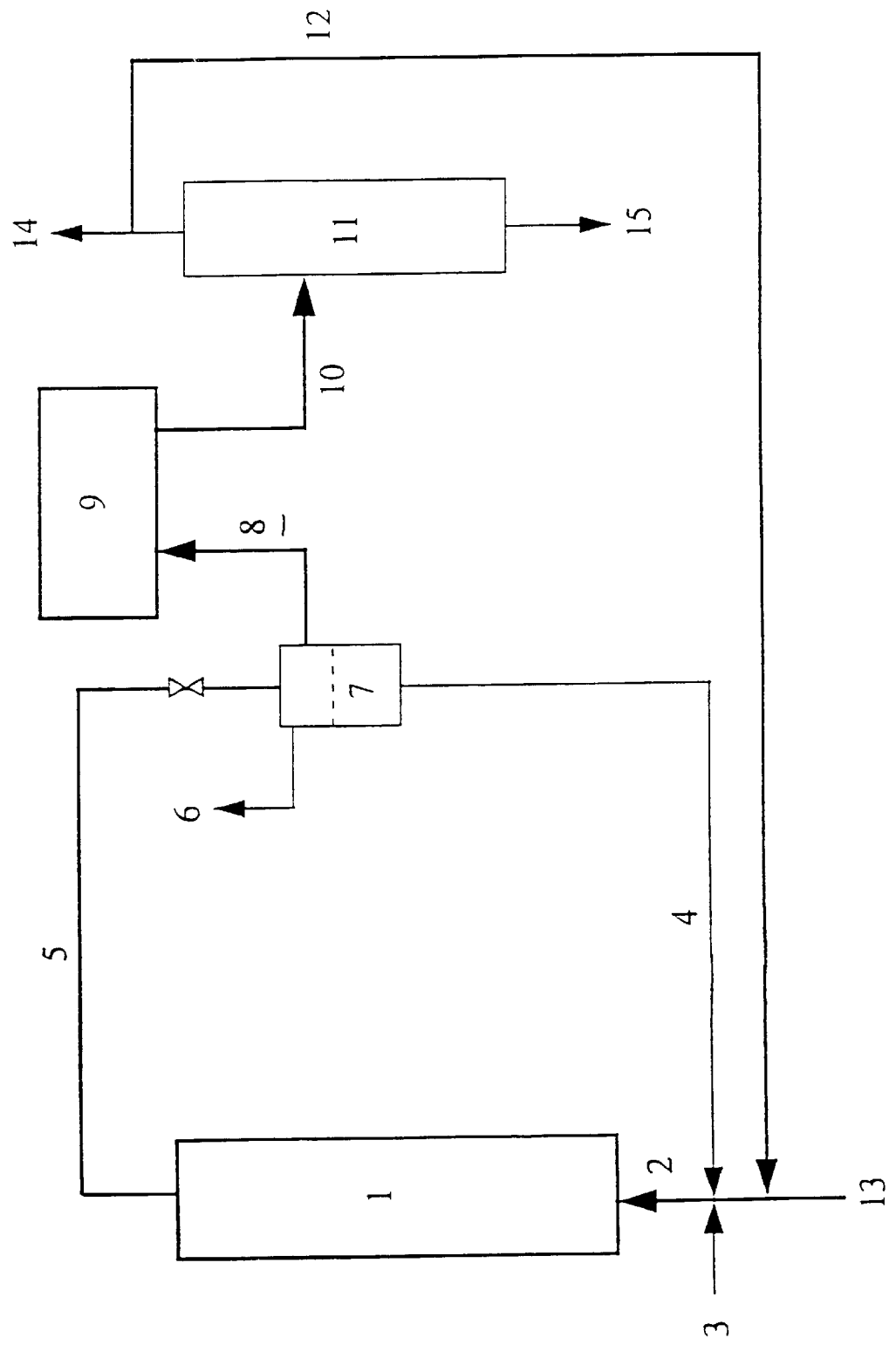

PROCESS FOR PREPARING HIGHER OXO ALCOHOLS FROM OLEFIN MIXTURES

BACKGROUND OF THE INVENTION

1. Field of the Invention

The present invention relates to a process for preparing higher oxo alcohols by hydroformylation of olefin mixtures, which includes selective hydrogenation of the hydroformylation mixtures and recycling of the unreacted olefins.

2. Discussion of the Background

Higher alcohols, and particularly those having 6 to 25 carbon atoms, may be prepared by the catalytic hydroformylation (or oxo reaction) of olefins having one less carbon atom and subsequent catalytic hydrogenation of the aldehyde- and alcohol-containing reaction mixtures. The alcohols are predominantly used as starting materials for the preparation of plasticizers or detergents.

The type of catalyst system and the optimum reaction conditions for the hydroformylation depend upon the reactivity of the olefin used. The dependence of the reactivity of the olefins on their structure is described, for example, by J. Falbe, New Syntheses with Carbon Monoxide, SpringerVerlag, Berlin, Heidelberg, N.Y., 1980, pages 95 ff. The varying reactivity, especially that of the isomeric octenes, is likewise known (B. L. Haymore, A. van Hasselt, R. Beck, Annals of the New York Acad. Sci., 415 (1983), pages 159–175). Industrial olefin mixtures that are used as starting materials for the oxo synthesis include olefin isomers a variety of structures and different having degrees of branching, different positions of the double bond in the molecule and different carbon numbers as well. This applies especially to olefin mixtures that have been produced by dimerization, trimerization or further oligomerization of $C_2$–$C_5$ olefins or other easily accessible higher olefins or by co-oligomerization of said olefins. Examples of typical isomeric olefin mixtures that can be reacted by rhodium or cobalt-catalyzed hydroformylation to give the corresponding aldehyde mixtures and alcohol mixtures include tripropenes, and tetrapropenes and dibutenes and tributenes.

The rate of the hydroformylation reaction decreases with increasing carbon number and with the degree of branching. The reaction rate of linear olefins can be greater than that of the branched isomers by a factor of 5 to 10. The position of the double bond in the olefin molecule also influences the reactivity. Olefins having a terminal double bond react markedly more rapidly than do isomers having the double bond in the interior of the molecule. Because of the differing reactivity of the olefin isomers, relatively long reaction times are required to achieve the highest possible conversion of the olefins. As a result, however, the product yield is decreased due to unwanted side reactions and secondary reactions. The same thing occurs if attempts are made to shorten the reaction times by higher reaction temperatures. Because of the varying reactivity of the isomers, it is especially difficult to achieve high conversion rates and simultaneously high selectivities in the hydroformylation of olefin mixtures.

SUMMARY OF THE INVENTION

An object of the invention is to provide a process for preparing higher oxo alcohols from the corresponding olefin mixtures, which combines high conversion rates with high selectivities and, in particular, high space-time yields.

These and other objects have been achieved by the present invention, which provides a process for preparing higher oxo alcohols, including hydroformylating a mixture of isomeric olefins having 5 to 24 carbon atoms in the presence of a catalyst in one stage, wherein the olefin conversion rate for one passage to is restricted to 40 to 90% to produce a reaction mixture, and selectively hydrogenating the reaction mixture, to produce a hydrogenation mixture.

Another embodiment of the present invention provides a composition, which includes a hydrogenation mixture produced by a process for preparing higher oxo alcohols, including:

hydroformylating of a mixture of isomeric olefins having 5 to 24 carbon atoms in the presence of a catalyst in one stage, wherein the olefin conversion rate for one passage to is restricted 40 to 90% to produce a reaction mixture, and selectively hydrogenating the reaction mixture, to produce the hydrogenation mixture.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein:

The figure shows the block diagram of a plant in which the process can be carried out continuously. The olefin mixture 2, synthesis gas (carbon monoxide and hydrogen) 3 and catalyst 4 are introduced into the reactor 1. The hydroformylation mixture 5 is expanded, the expansion gas 6 (unconsumed synthesis gas) is taken off and the expanded hydroformylation mixture is freed, in the catalyst removal step 7, from the catalyst 4 which, if appropriate after supplementation by fresh catalyst, is recirculated to the reactor 1. The hydroformylation mixture 8 freed from the catalyst is passed into the hydrogenation 9 in which the aldehydes and also acetals of the aldehydes and esters of the alcohols, in particular their formates, present as byproducts, are hydrogenated to the alcohols. In the distillation stage 11, the low-boilers 12 are separated off from the hydrogenation mixture 10, which low-boilers very predominantly consist of unreacted isomeric olefins and are conducted, together with fresh olefins 13, into the reactor 1 as olefin mixture 2. Some of the low-boilers can be taken off from the olefin circuit as residual low-boilers 14. The crude alcohol mixture 15 is worked up to pure alcohol in a further distillation stage which is not shown.

BRIEF DESCRIPTION OF THE PREFERRED EMBODIMENTS

A more complete appreciation of the invention and many of the attendant advantages thereof will be readily obtained as the same becomes better understood by reference to the following detailed description when considered in connection with the accompanying drawings, wherein:

Preferably, the process according to the invention can be carried out batchwise, but a continuous procedure is more preferred.

Preferably, the reaction mixture is selectively hydrogenated, after the catalyst is removed, the hydrogenation mixture is separated by distillation, and the olefin fraction is recirculated to the hydroformylation.

Hydroformylation

Preferably, the starting materials for the hydroformylation are mixtures of monoolefins having from 5 to 24 carbon atoms and a terminal or middle-position C—C double bond, such as 1- or 2-pentene, 2-methyl-1-butane, 1-, 2- or 3-hexene, the isomeric $C_6$ olefin mixture (dipropene) produced in the dimerization of propene, 1-heptene, 2- or 3-methyl-1-hexene, 1-octene, the isomeric $C_8$ olefin mixture (dibutene) produced in the dimerization of butenes, 1-nonene, 2-, 3- or 4-methyl-1-octane, the isomeric $C_9$ olefin mixture (tripropene) produced in the trimerization of propene, 1-, 2- or 3-decene, 2-ethyl-1-octene, 1-dodecene, the isomeric $C_{12}$ olefin mixture (tetrapropene or tributene) produced in the tetramerization of propene or the trimerization of butenes, 1-tetradecene, 1- or 2-hexadecene, $C_{16}$ olefin mixtures (tetrabutene) produced in the tetramerization of butenes, and olefin mixtures prepared by cooligomerization of olefins having different carbon numbers (preferably 2 to 4), if appropriate after separating off by distillation into fractions of identical or similar carbon number. Especially preferred starting materials are $C_8$, $C_9$, $C_{12}$, or $C_{16}$ olefin mixtures.

The type or the conditions of the hydroformylation are not particularly limited and, rather, the olefins may be hydroformylated in a manner known per se. Accordingly, rhodium catalysts or preferably cobalt catalysts are therefore employed, with or without complex-stabilizing additions, such as organic phosphines or phosphites. The temperatures and the pressures can vary within broad ranges, depending on the catalyst and the olefin mixture. A description of the hydroformylation of olefins is given, for example, in J. Falbe, New Syntheses with Carbon Monoxide, Springer-Verlag, Heidelberg, N.Y., 1980, pages 99 ff., and in Kirk-Othmer, Encyclopedia of Chemical Technology, Volume 17, 4th edition, John Wiley & Sons, pages 902–919 (1996), the entire contents of which are hereby incorporated by reference.

In the process according to the invention, the degree of conversion for one pass is restricted to from 40 to 90%. Preferably, from 65 to 80% of the olefins are converted. The preferred starting materials are $C_8$, $C_9$, $C_{12}$ or $C_{16}$ olefin mixtures, which contains a great number of different isomers. As mentioned above, straight-chain olefins having terminal olefinic double bonds react most readily. Therefore, the reactivity decreases the more extensively the molecule is branched and/or the further the double bond is in the interior of the molecule. Surprisingly, the restriction on conversion rate according to the invention has the effect that the reactive olefins preferentially react to completion, while the less reactive olefins remain in the reaction mixture and, after the selective hydrogenation of the reaction mixture, are recirculated to the hydroformylation. Surprisingly, the restriction of conversion rate increases the selectivity of the hydroformylation. Olefin recycling increases the total residence time of the less-reactive olefins. As a consequence of the olefin recycling, higher overall olefin conversion rates with reduced byproduct formation and thus higher aldehyde yields are achieved and, after hydrogenation, higher alcohol yields are achieved. In addition, the smaller amount of byproducts facilitates work-up of the reaction mixtures. In comparison with single stage processes without olefin recycling, the process according to the invention, owing to the selective hydrogenation and olefin recycling, increases the economic efficiency of the preparation of oxo alcohols.

Preferably, the degree of conversion of the olefins may be restricted to the desired value by changing appropriately the hydroformylation reaction conditions. By selecting lower reaction temperatures and/or catalyst concentrations as well as shorter reaction times, the olefin conversion rate can be decreased. The degree of conversion for one passage of the olefin mixture 2 (=fresh olefin mixture 13+recirculated low-boilers 12 is determined on the basis of the amount and composition of the olefin mixture 2 and on the amount and composition of the recirculated low-boilers 12 plus the withdrawn low-boilers 14. The overall degree of conversion is determined on the basis of the amount and composition of the fresh olefin mixture 13 and on the amounts of olefin discharged with the residual low-boilers 14. To determine the olefin contents in the various streams, gas-chromatographic analysis can be employed.

Catalyst Removal

The hydroformylation reaction mixtures are preferably freed from the catalyst first, again in a manner known per se. If a cobalt catalyst was used, this can be achieved by pressure reduction, separating off the aqueous catalyst phase, oxidizing with air or oxygen the cobalt carbonyl compounds remaining in the hydroformylation mixture and extracting the resulting cobalt compounds with water or aqueous acid. Cobalt-depletion processes are well known, see, for example, J. Falbe, loc. cit., 164, 165 (BASF Process), Kirk-Othmer, loc. cit. and EP-0 850 905 A1, the entire contents of each of which are hereby incorporated by reference. If a rhodium compound served as hydroformylation catalyst, it can be removed from the hydroformylation mixture as distillation residue by means of thin-film evaporation.

Preferably, the hydroformylation reaction mixtures, freed from catalyst and depending on the degree of conversion, contain 3–40% by weight, more preferably 5 to 30% by weight, of low-boilers having a boiling point lower than the aldehydes. The low-boilers preferably include olefins, the corresponding saturated hydrocarbons, water and, optionally, methanol. The hydroformylation reaction mixtures contain further 30–90% by weight of aldehydes, 5–60% by weight of alcohols and up to 10% by weight of formates of these alcohols. In addition, the hydroformulation reaction mixtures contain further 5–15% by weight of high-boilers having a boiling point higher than the alcohols, for example carboxylic acids, esters or aldolisation products. Hydroformylation mixtures having compositions other than those described above may also be used.

Selective Hydrogenation

The selective hydrogenation of the hydroformylation mixtures freed from the hydroformylation catalyst is most preferred. In the hydrogenation, the aldehydes and certain accompanying substances, including acetals of the aldehydes and esters of the alcohols, and of these particularly the formates, are hydrogenated to the desired alcohols. Since the conversion rate in the hydroformylation stage is restricted, it is most preferred for the economic efficiency of the process that in the hydrogenation the unreacted olefins are not hydrogenated, or are virtually not hydrogenated, so that they can be separated off from the hydrogenation mixture and recirculated to the hydroformylation.

Selective hydrogenation of hydroformylation mixtures is described in the co-pending patent application DE 198 42 370.5, the entire contents of which are hereby incorporated by reference. The hydroformylation reaction mixtures are preferably hydrogenated by means of hydrogen at elevated temperature and at elevated pressure at a supported catalyst which includes as active components, copper, nickel and chromium.

Preferred supported catalysts include, as active components, copper and nickel at concentrations independently in each case of from 0.3 to 15% by weight, chromium at a concentration of from 0.05 to 3.5% by weight and an alkali metal component at a concentration of from 0.01 to 1.6% by weight, more preferably 0.02–1.2% by weight, in each case based on the supported catalyst. Another preferred supported catalyst includes copper, nickel and chromium in the specified amounts, but no alkali metal component. Preferred support substances are silicon dioxide and aluminum oxide. The amounts specified are based on the catalyst, which is prepared as described below and which has not yet been reduced.

In the hydrogenation, the aldehydes in the hydroformylation mixtures are preferably hydrogenated to the corresponding alcohols in only one hydrogenation stage at conversion rates greater than 98% at a selectivity of greater than 99%. The esters and acetals are likewise converted into the desired alcohols. The starting olefins present in the mixture remain surprisingly unchanged for the most part, although the preferred supported catalysts, under comparable conditions, also hydrogenate almost quantitatively the olefinic double bond in 2-ethylhex-2-enal (EP 0 326 674 A2, the entire contents of which are hereby incorporated by reference). The hydrogenation may preferably be carried out in the low-pressure region of below 30 bar and at high space-time yields.

The catalyst components can be distributed homogeneously in the pores of a support material or enriched in its edge zones. In the former case, an aqueous solution is made up which contains the components in the form of metal salts as catalyst precursor and whose volume preferably corresponds to roughly 0.8 times the pore volume of the support material. Preferred copper salts, nickel salts and chromium salts include those which are converted on heating into oxides, such as nitrates and acetates. If the catalyst is to contain an alkali metal component, this can be introduced together with chromium in the form of alkali metal chromate or alkali metal bichromate, preferably as sodium chromate or sodium bichromate. The metal salt concentration in the solution depends on the desired concentration of the respective component in the finished catalyst. The metal salt solution is then sprayed onto the non-preheated support material, situated in a coating drum and penetrates into the pores thereof. The catalyst is then dried.

If it is desired to have a catalyst with components which are enriched in the edge zones of a porous or a more or less pore-free support material, the metal salt solution can be sprayed onto a preheated support material and the support material can be further heated during the spraying, so that the water evaporates and the catalyst components are fixed substantially on the surface of the support material.

After the catalyst components are applied, the catalysts of both types are calcined, i.e. depending on the catalyst precursor used, heated to temperatures of 200–400° C., the catalyst precursors being converted to the oxides. The catalyst is then reduced with hydrogen. The reduction can be performed just after the catalyst is prepared or preferably not until the hydrogenation reactor.

The catalysts are preferably used in a form in which they offer a low resistance to flow, e.g. in the form of granules, pellets or shaped bodies such as tablets, cylinders, rod extrudates or rings. They are preferably activated prior to use by heating in a hydrogen stream, e.g. at hydrogenation temperatures from 150 to 250° C. if they have not been reduced in the reactor.

The hydrogenation can be carried out continuously or batchwise and either in the gas phase or in the liquid phase. Hydrogenation in the liquid phase is preferred, since the gas-phase process requires a higher energy consumption because of the necessary circulation of large gas volumes. In addition, evaporating aldehydes having an increasing carbon number requires more and more energy, and the starting material loading in the reduction gas decreases, so that a gas-phase process in the case of aldehydes having a carbon number greater than about 8 makes it difficult to carry out the overall process economically.

Various process variants can be selected for the liquid-phase hydrogenation. It can be carried out adiabatically or virtually isothermally, i.e. having a temperature rise of <10° C., and either in a single stage or two stages. In the latter case, both reactors, and preferably tube reactors, can be operated adiabatically or virtually isothermally, or one can be operated adiabatically and the other virtually isothermally. In addition, it is possible to hydrogenate the hydroformylation mixtures in a straight pass or with product recycling. The reactors can be operated as concurrent flow reactors with a trickle bed (trickle flow) or preferably with high liquid loadings (pulse flow). In the interest of a high space-time yield, the reactors are preferably operated with high liquid loadings of 5–100 m$^3$, more preferably 15–50 m$^3$ per m$^2$ of cross section of the empty reactor and hour. If the reactor is operated isothermally and in a straight pass, the catalyst space velocity (LHSV) values are preferably between 0.1 and 10 h$_{-1}$, and more preferably between 0.5 and 5 h$_{-1}$.

The liquid-phase hydrogenation is preferably carried out at an overall pressure of from 5 to 30 bar, more preferably between 15 and 25 bar. The gas-phase hydrogenation can also be carried out at lower pressures, with correspondingly greater gas volumes. The reaction temperatures, in the case of hydrogenations in the liquid or gas phase, are preferably between 120 and 220° C., in particular between 140 and 180° C.

Separation of the Hydrogenation Mixture by Distillation

After the hydrogenation, the reaction mixtures are preferably worked up by distillation in a manner known per se. This is preferably performed under reduced pressure, e.g. at an absolute pressure of from 400 to 900 mbar. In the distillation, the olefins are recovered as by far the most predominant constituent of the low-boiler fraction. Preferably, the majority of the low boiler fraction, generally from 60 to 98%, is recirculated to the hydroformylation. The remaining portion of the low-boiler fraction, that is from 2 to 40%, can be discharged from the olefin circuit so that the concentration of the inert saturated hydrocarbons, which have been formed by hydrogenation of the olefins in the hydroformylation stage, does not exceed 70%, and preferably is kept below 60%.

EXAMPLES

Having generally described this invention, a further understanding can be obtained by reference to certain specific examples, which are provided herein for purposes of illustration only and are not intended to be limiting unless otherwise specified.

Comparison Example

Hydroformylation of di-n-butene

In a 5-liter high-pressure autoclave equipped with a stirrer and electric heater, there was hydroformylated 2000 g of di-n-butene (C$_8$ olefin from the OXENO Octol process) in the presence of a cobalt catalyst at 180° C., with synthesis-gas pressure kept constant at 280 bar. The synthesis gas contained 50 vol% CO and 50 vol% H$_2$.

An aqueous cobalt acetate solution containing 0.95 wt% of Co was used as catalyst precursor to synthesize the cobalt hydride carbonyls used as catalyst. The cobalt acetate solution was treated with synthesis gas under stirring for 7 hours at 170° C. and 280 bar. After cooling to room temperature and depressurization, the formed cobalt hydride carbonyls were transferred to the organic phase by extraction with the di-n-butene educt. After separation of the aqueous phase, the di-n-butene containing cobalt hydride carbonyls in a concentration of 0.025 wt% Co (calculated as the metal) was hydroformylated for 3 hours under the aforementioned reaction conditions.

After cooling to room temperature, the reaction mixture was depressurized, emptied from the autoclave and freed of Co catalyst by treatment with 5% acetic acid and air at 80° C. There was obtained 2488 g of hydroformylation mixture, which was analyzed by means of gas chromatography (GC). The results are presented in Table 1. They indicate that di-n-butene conversion of 89.3% had been achieved with a selectivity relative to valuable product of 90.7%, corresponding to an 81.0% yield of valuable product relative to di-n-butene starting material. $C_8$ aldehydes, $C_9$ alcohols and isononyl formate are considered to be valuable products.

Example (according to the Invention)
Hydroformylation of di-n-butene with Recycled C8 Olefin 2488 g of the hydroformylation mixture from the comparison example was hydrogenated selectively while preserving the olefins to obtain the $C_9$ alcohol as valuable product. The hydrogenation process was performed in batches in a 5-liter autoclave at 80° C. and 20 bar $H_2$ pressure in the liquid phase in the presence of a supported catalyst comprising 12.1 wt% Cu, 3.0 wt% Ni and 2.5 wt% Cr on alumina as support material. In a laboratory distillation column, the unreacted olefins were then distilled off from the hydrogenation mixture as volatiles to separate them from the valuable products and the low-boiling fraction.

There was obtained 250 g of a volatiles fraction, which according to GC analysis contained, in addition to 98.7 wt% $C_8$ hydrocarbons, 78.4 wt% of which was $C_8$ olefins, around 1.3 wt% methanol (secondary product of hydrogenation of isononyl formate). The volatiles fraction and 2000 g of di-n-butene, or in other words 2250 g of educt in total containing 2193 g of $C_8$ olefin, was hydroformylated in a 5-liter autoclave at 180° C. and a synthesis-gas pressure of 280 bar in the presence of a cobalt catalyst by the technique described in the comparison example. A synthesis gas containing 50 vol% CO and 50 vol% $H_2$ was again used. This mixture was hydroformylated for 3 hours at a cobalt concentration of 0.024 wt% relative to the $C_8$ olefin mixture.

After cooling to room temperature, the reaction mixture was depressurized, emptied from the autoclave and freed of Co catalyst by treatment with 5% acetic acid and air at 80° C. There was obtained 2731 g of hydroformylation mixture, which was analyzed by means of gas chromatography. The results are presented in Table 1. They indicate 88.2% $C_8$ olefin conversion with a selectivity relative to valuable product of 90.9%, corresponding to an 80.2% yield of valuable product relative to the $C_8$ olefin starting material. $C_8$ aldehydes, $C_9$ alcohols and isononyl formate were again considered to be valuable products.

In order to be able to appraise the influence, on yield of valuable product, of olefin recycling according to the present invention, the yield relative to $C_8$ olefin (di-n-butene and $C_8$ recycle olefin) was calculated relative to the starting quantity of fresh di-n-butene (2000 g). In this way the yield relative to di-n-butene was found to be 88.0%. Compared with hydroformylation without olefin recycling according to the Comparison Example, an increase in yield of valuable product of around 8% is achieved by olefin recycling. In practice, the $C_8$ paraffins and part of the $C_8$ olefins are transferred out by purging during the continuous operating process.

TABLE 1

| Composition of hydroformylation mixtures | | |
|---|---|---|
| Composition according to GC analysis | Comparison Example, wt % | Example, wt % (without paraffins of the 1st hydroformylation cycle) |
| $C_8$ olefins | 8.6 | 9.5 |
| $C_8$ paraffins | 2.2 | 2.0; only paraffins of the 2nd hydroformylation cycle |
| Isononanals | 55.8 | 57.0 |
| Ester/isononyl formate | 4.5 | 4.8 |
| Isononanol | 23.4 | 21.2 |
| Residue | 5.5 | 5.5 |

Accordingly, in a one-stage process, the yield of valuable materials can no longer be significantly improved by higher conversion of di-n-butene, since a drop in selectivity is caused by secondary reactions when the conversion is increased.

In contrast, the process according to the invention permits higher conversion of di-n-butene to valuable products without loss of selectivity.

Having now fully described the invention, it will be apparent to one of ordinary skill in the art that many changes and modifications can be made thereto without departing from the spirit or scope of the invention as set forth herein.

This application is based on German Patent Application DE 19842371.3, filed Sept. 16, 1998, the entire contents of which are hereby incorporated by reference.

What is claimed is:

1. A process for preparing higher oxo alcohols, comprising
    hydroformylating a mixture of isomeric olefins having 5 to 24 carbon atoms in the presence of a catalyst in one stage, wherein the olefin conversion rate for one passage to is restricted to 40 to 90% to produce a reaction mixture, and
    selectively hydrogenating the reaction mixture, to produce a hydrogenation mixture.

2. The process as claimed in claim 1, wherein the mixture of isomeric olefins comprise at least one olefin selected from the group consisting of $C_8$, $C_9$, $C_{12}$ or $C_{16}$ olefins.

3. The process as claimed in claim 1, wherein the reaction mixture is hydrogenated at elevated temperature and at elevated pressure at a supported catalyst which comprises, as active components, copper, nickel and chromium.

4. The process as claimed in claim 3, wherein the supported catalyst comprises, as active components, copper and nickel at concentrations independently in each case of 0.3 to 15% by weight, chromium at a concentration of 0.05 to 3.5% by weight and an alkali metal at a concentration of 0.01 to 1.6% by weight, in each case based on weight of the supported catalyst.

5. The process as claimed in claim 4, wherein the concentration of the alkali metal is 0.2 to 1.2% by weight.

6. The process as claimed in claim 1, wherein the supported catalyst does not contain an alkali metal.

7. The process as claimed in claim 1, wherein the catalyst is a supported catalyst comprising a support material selected from the group consisting of silicon dioxide and aluminum oxide, and mixtures thereof.

8. The process as claimed in claim 7, wherein the active components are homogeneously distributed in the pores of the support material.

9. The process as claimed in claim 7, wherein the active components are homogeneously enriched in the edge zones of the support material.

10. The process as claimed in claim 1, wherein the hydrogenating is carried out continuously or batchwise in the liquid phase.

11. The process as claimed in claim 1, wherein the hydrogenating is carried out in the liquid phase at an overall pressure of 5 to 30 bar.

12. The process as claimed in claim 11, wherein the overall pressure is 15 to 25 bar.

13. The process as claimed in claim 1, wherein the hydrogenating is carried out at a temperature of 120 to 220° C.

14. The process as claimed in claim 13, wherein the temperature is 140 to 180° C.

15. The process as claimed in claim 1, wherein the hydrogenating is carried out in the liquid phase and at liquid loadings of 5–100 m$^3$ per m$^2$ of cross section of the empty reactor and hour.

16. The process as claimed in claim 15, wherein the liquid loading is 15–50 m$^3$ per m2 of cross section of the empty reactor and hour.

17. The process as claimed in claim 1, further comprising separating the hydrogenation mixture from a low-boiler fraction comprising unreacted olefins by distillation and recirculating the unreacted olefins to the hydroformylating.

18. The process as claimed in claim 17, further comprising discharging 2 to 40% of the low-boiler fraction.

19. The process as claimed in claim 1, further comprising removing the catalyst prior to hydrogenating the reaction mixture.

20. The process as claimed in claim 1, further comprising separating an olefin fraction from the hydrogenation mixture and recirculating the olefin fraction to the hydroformylating.

21. A composition, comprising a hydrogenation mixture produced by a process for preparing higher oxo alcohols, comprising hydroformylating of a mixture of isomeric olefins having 5 to 24 carbon atoms in the presence of a catalyst in one stage, wherein the olefin conversion rate for one passage to is restricted 40 to 90% to produce a reaction mixture, and selectively hydrogenating the reaction mixture, to produce the hydrogenation mixture.

* * * * *